United States Patent
Koroskenyi et al.

(10) Patent No.: US 8,378,038 B2
(45) Date of Patent: Feb. 19, 2013

(54) POLYSILOXANE BLOCK COPOLYMERS

(75) Inventors: Balint Koroskenyi, Sleepy Hollow, NY (US); Manuel Gamez-Garcia, New City, NY (US); Jianwen Mao, New Milford, CT (US)

(73) Assignee: BASF SE, Ludwigshafen (DE)

( * ) Notice: Subject to any disclaimer, the term of this patent is extended or adjusted under 35 U.S.C. 154(b) by 57 days.

(21) Appl. No.: 12/830,106

(22) Filed: Jul. 2, 2010

(65) Prior Publication Data

US 2010/0303750 A1  Dec. 2, 2010

Related U.S. Application Data

(62) Division of application No. 12/012,063, filed on Jan. 31, 2008, now abandoned.

(51) Int. Cl.
*C08F 283/12* (2006.01)
(52) U.S. Cl. .......................... 525/479; 526/310
(58) Field of Classification Search .................. 525/479; 526/310
See application file for complete search history.

(56) References Cited

U.S. PATENT DOCUMENTS

| | | | |
|---|---|---|---|
| 5,302,322 A | 4/1994 | Birtwistle | 252/547 |
| 5,573,709 A | 11/1996 | Wells | 510/122 |
| 5,760,136 A | 6/1998 | Kato et al. | 525/100 |
| 5,977,038 A | 11/1999 | Birtwistle et al. | 510/122 |
| 6,200,554 B1 | 3/2001 | Yeoh et al. | 424/70.12 |
| 6,201,093 B1 | 3/2001 | Messner et al. | 528/28 |
| 6,451,298 B1 | 9/2002 | Decoster et al. | 424/70.12 |
| 2003/0225168 A1 | 12/2003 | Deroo et al. | 516/77 |
| 2004/0009136 A1 | 1/2004 | Dubief et al. | 424/70.11 |
| 2004/0039101 A1 | 2/2004 | Dubief et al. | 524/505 |
| 2004/0202634 A1 | 10/2004 | L'Alloret | 424/70.16 |
| 2005/0002871 A1 | 1/2005 | Ivanova et al. | 424/47 |
| 2006/0123564 A1 | 6/2006 | Nishizawa et al. | 8/405 |
| 2006/0217285 A1 | 9/2006 | Destarac | 510/475 |
| 2007/0106045 A1 | 5/2007 | Lange et al. | 528/29 |

FOREIGN PATENT DOCUMENTS

| | | |
|---|---|---|
| DE | 102005018315 | 11/2006 |
| JP | 1995/002964 | 1/1995 |
| JP | 1998/291967 | 11/1998 |
| JP | 2007 124993 | * 5/2007 |
| WO | 99/32539 | 7/1999 |
| WO | 02/10501 | 2/2002 |

OTHER PUBLICATIONS

JP 2007 124993 Machine translation.*

* cited by examiner

*Primary Examiner* — Kuo-Liang Peng
(74) *Attorney, Agent, or Firm* — Shiela Loggins

(57) ABSTRACT

This invention encompasses novel amphiphilic block copolymers comprising polysiloxane blocks and polycationic blocks. The polycationic blocks are formed from diallyl-dialkylammonium derivatives. The formed block copolymers are particularly useful for treating or conditioning keratinous substances such as hair or skin.

14 Claims, No Drawings

POLYSILOXANE BLOCK COPOLYMERS

This application is a divisional of U.S. Ser. No. 12/012,063 which takes the benefit of U.S. Provisional Application Nos. 60/899,675, filed Feb. 6, 2007, all herein incorporated entirely by reference.

FIELD OF THE INVENTION

This invention relates to novel amphiphilic block copolymers comprising polysiloxane blocks and polycationic blocks. The polycationic blocks are formed from diallyldialkylammonium derivatives. The formed block copolymers are particularly useful for treating or conditioning keratinous substances such as hair or skin.

BACKGROUND OF THE INVENTION

Conditioning shampoos both clean and condition the hair in one step. However, prior means of achieving both the cleansing and the conditioning of hair in one step are problematic. Normally the conditioning agent, frequently a siloxane, will wash out with the rinse water because of the detersive action of surfactants also incorporated into the shampoo. In order to solve this problem, deposition agents such as cationic polymers may be combined with the conditioning agent in the shampoo to more effectively bind the conditioning agent onto the hair and thus resist wash out in the rinse cycle. Such combinations are disclosed in U.S. Pat. Nos. 5,573,709, 5,977,038, 6,200,554, 6,451,298 and 5,302,322 and U.S. Application Publication Nos. 2006/0123564 and 2005/0002871 herein incorporated entirely by reference.

This solution, however, is not entirely adequate and there is still much room for improvement in conditioning shampoos. For example, many cationic polymers tend to build up on the hair and to result in an undesirable, "unclean" coated feel. Cationic polymers therefore, conventionally, are preferably used at limited levels to minimize this problem. This, however, can limit the overall conditioning benefits that are obtained. Furthermore, the use of two separate ingredients (cationic polymer and silicone) has a high adverse impact on cost of the shampoo formulation; the levels of hair conditioning wet lubricity are not comparable to those obtained from a rinse off conditioner and frequently the silicone/cationic polymers complex in the shampoo giving an opaque formulation.

The presently disclosed amphiphilic block copolymer comprising polysiloxane and polycationic blocks resolves many of the above problems associated with the present state of the art for conditioning shampoos.

Amphiphilic block copolymers are however, generally known for use in cosmetics. These amphiphilic block copolymers comprise hydrophobic and hydrophilic segment and are described in U.S. Application Nos. 2003/0225168, 2004/0039101, 2004/0009136, 2006/0217285 and 2004/0202634 herein incorporated entirely by reference.

Cationic functionalized polysiloxanes are also known and are disclosed in Japanese unexamined Application Nos. JP1995002964 and JP1998291967 and PCT Application No. WO99/32539. These modified polysiloxanes are known for use as conditioning agents in hair bleach or dye compositions such as disclosed in U.S. Application Publication No. 2006/0123564 herein incorporated entirely by reference.

Furthermore, block copolymers formed from polysiloxanes and polycationic segments are known such as those described in U.S. Pat. No. 5,760,136 herein incorporated entirely by reference. This reference does not disclose block copolymers comprising polysiloxane blocks and polycationic blocks derived from diallydialkylammonium monomers.

Thus, the inventors believe the presently disclosed amphiphilic block copolymers formed from polysiloxanes and a polycationic blocks wherein the polycationic block is derived from diallydialkylammonium monomers to be novel and to provide optimal cleaning and conditioning of keratinous substrate (hair and skin) while reducing the number of undesirable side effects that can result from conditioning agent build-up.

SUMMARY OF THE INVENTION

The invention is directed to an amphiphilic block copolymer; a conditioning shampoo comprising the amphiphilic block copolymer; an amphiphilic block copolymer keratinous substrate conditioning agent and an amphiphilic block copolymer keratinous substrate conditioning deposition aid.

Thus
the invention is directed to an amphiphilic block copolymer comprising:

a) a siloxane block polymer of formula (I)

wherein n is a number between 2 and 10,000,
and
b) a cationic block polymer formed from at least a cationic monomer of formula (II)

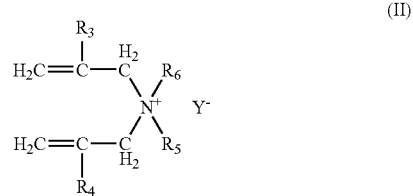

wherein $R_3$ and $R_4$ are independently of one another hydrogen or $C_1$-$C_4$ alkyl; $R_5$ and $R_6$ are, independently, hydrogen or an alkyl, hydroxyalkyl, carboxyalkyl, carboxyamidalkyl or alkoxyalkyl groups having from 1 to 18 carbon atoms; and $Y^-$ represents an anion.

For example, the amphiphilic block copolymer comprises
a) a siloxane block polymer of formula (I)

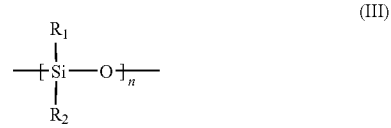

wherein $R_1$ and $R_2$ are independently alkyl, alkoxy, phenylalkyl, aryl, aryloxy, alkylaryl, alkylamine, alkylhydroxy, polyoxyalkylene and polyalkylene polyamine, n is a number between 2 to 10,000 b) a cationic block polymer formed from at least a cationic monomer of formula (II)

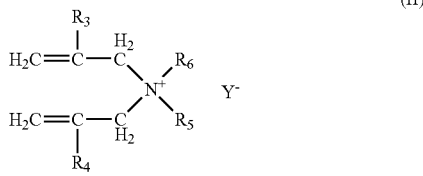

wherein $R_3$ and $R_4$ are independently of one another hydrogen or $C_1$-$C_4$ alkyl; $R_5$ and $R_6$ are, independently, hydrogen or an alkyl, hydroxyalkyl, carboxyalkyl, carboxyamidalkyl or alkoxyalkyl groups having from 1 to 18 carbon atoms; and $Y^-$ represents an anion.

The amphiphilic block copolymer may also be defined by the structure below

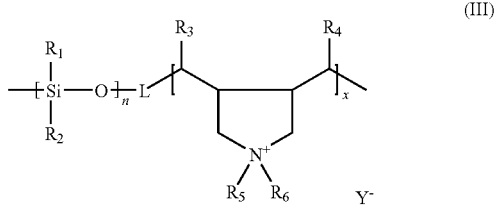

wherein $R_1$, $R_2$, $R_3$, $R_4$, $R_5$, $R_6$, n and $Y^-$ are defined as above, x is an integer between 2 and 1000 and L is a linking group.

A linking group for purposes of the invention is at least a divalent linking group. The linking group may also contain a heteroatom such as sulfur, nitrogen, oxygen or combinations thereof.

The linking group will preferably contain a derivative of a chain transfer agent.

For example, if the siloxane block polymer terminates in a thiol, it will react to form a covalent link with the cationic block polymer. Thus the linking group in the formed amphiphilic block copolymer will then contain a thio ether, a derivative of thiol.

For example, the linking group of formula (III) may be as below:

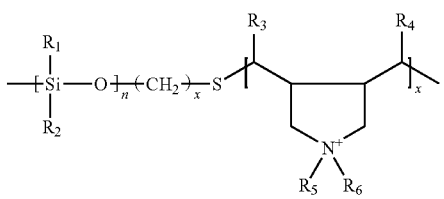

Furthermore, the invention encompasses
a hair conditioning shampoo composition comprising:
a) an amphiphilic block copolymer comprising at least
   i.) a siloxane block polymer of formula (I)
   and
   ii.) a cationic block polymer formed from at least a cationic monomer of formula (II)
and
b) a detersive surfactant.

Additionally, a keratinous substrate conditioner or keratinous substrate conditioner deposition aid comprising the amphiphilic block copolymer described above are embodiments of the invention.

Several methods are embodied in the present invention.

The first method is directed to the preparation of an amphiphilic block copolymer comprising
a siloxane block polymer of formula (I)
and
a cationic block polymer formed from at least a cationic monomer of formula (II)
the method of preparation comprising the steps of polymerizing the cationic monomer of formula (II) in the presence of the siloxane polymer block of formula (I)
and
an initiator,
wherein the siloxane block polymer is terminated with a chain transfer group.

A second method is directed to a method of conditioning a keratinous substrate by applying an amphiphilic block copolymer comprising
a siloxane block polymer of formula (I)
and
a cationic block polymer formed from at least a cationic monomer of formula (II) onto the substrate.

DETAILED DESCRIPTION OF THE INVENTION

Definitions

All percentages, parts and ratios are based upon the total weight of the shampoo compositions of the present invention, unless otherwise specified. All such weights as they pertain to listed ingredients are based on the active level and, therefore, do not include carriers or by-products that may be included in commercially available materials, unless otherwise specified.

Keratinous substrate is hair, skin, finger nails or toe nails.

Amphiphilic block copolymers are normally defined as block copolymers comprising hydrophobic and hydrophilic blocks.

"Block copolymers" as used herein is meant to encompass two or more different polymeric units which are linked to form a single polymer molecule. Typically, the block copolymers are in the form of di-, tri- and multi-block polymers. The block copolymers may be linear, grafted, comb or star architecture.

For purposes of the invention the term "polymer block" refers to one of the blocks of the block copolymer. The polymer block is either hydrophilic or hydrophobic. The polymer block may be random or made up of blocks.

For example, the block copolymer may be (a cationic polymer block-siloxane polymer block) diblock copolymer, a (cationic polymer block-siloxane polymer block-cationic polymer block) a triblock copolymer.

The terms "hydrophobic" and "hydrophilic," when applied to the block copolymers of this invention, are used in their ordinary sense. That is, hydrophilic, when it refers to a polymer, means that the polymer has a strong tendency to bond with or absorb water, which can result in solution of the polymer or swelling and/or formation of a gel. This property is characteristic of polymers prepared from polar or ionic monomers. Similarly, hydrophobic, when it refers to hydrophobic block, means that the polymer is antagonistic to water and generally cannot be dissolved in or swelled by water. This property is characteristic of polymers prepared from relatively non-polar monomers.

The hydrophobic block is derived from siloxane containing monomers which may be slightly soluble in water. The important attribute of the siloxane hydrophobic block is once it is formed, the resulting block is insoluble or not swellable in water. The hydrophobic or siloxane polymer block may be formed from additional ethylenically unsaturated monomers. The hydrophobic or siloxane polymer block may also be grafted, further functionalized and/or crosslinked.

The hydrophilic block of the amphiphilic block copolymer of the invention is derived from diallydialkylammonium monomers. The amphiphilic block may be formed from diallylamine, then quaternized. The hydrophilic block may also be formed from additional ethylenically unsaturated monomers which are ionic and/or nonionic, as long as the hydrophilic polymer block maintains its hydrophilic properties. The hydrophilic polymer block may also be grafted, random or further functionalized and/or crosslinked.

The formed amphiphilic block copolymers of the invention may be grafted, crosslinked, linear or structured.

The terms structured and unstructured is often used to refer to the crosslinking character of a formed polymer.

The amphiphilic block copolymer of the invention comprises at least two polymer blocks or segments.

The hydrophobic or siloxane polymer block is a block of formula (I)

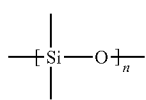
(I)

wherein n is a number between 2 and 10,000,
and
the hydrophilic block is a
a cationic polymer block formed from at least a cationic monomer of formula (II)

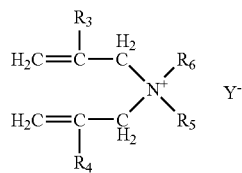
(II)

wherein $R_3$ and $R_4$ are independently of one another hydrogen or $C_1$-$C_4$ alkyl; $R_5$ and $R_6$ are, independently, hydrogen or an alkyl, hydroxyalkyl, carboxyalkyl, carboxyamidalkyl or alkoxyalkyl groups having from 1 to 18 carbon atoms; and $Y^-$ represents an anion.

Thus the polysiloxane may have almost any substitution.

A more specific example of the amphiphilic block copolymer may comprise
a) a siloxane block polymer of formula (III)

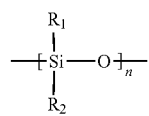
(III)

wherein $R_1$ and $R_2$ are independently alkyl, phenylalkyl, alkoxy, aryl, aryloxy, alkylaryl, alkylamine, alkylhydroxy, polyoxyalkylene and polyalkylene polyamine, n is a number between 2 to 10,000.
and
b) a cationic block polymer formed from at least a cationic monomer of formula (II)

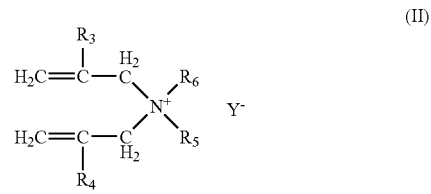
(II)

wherein $R_3$ and $R_4$ are independently of one another hydrogen or $C_1$-$C_4$ alkyl; $R_5$ and $R_6$ are, independently, hydrogen or an alkyl, hydroxyalkyl, carboxyalkyl, carboxyamidalkyl or alkoxyalkyl groups having from 1 to 18 carbon atoms; and $Y^-$ represents an anion.

The Siloxane Polymer Block

The siloxane polymer block or segment may be formed from additional monomers. The additional monomers may or may not contain silicon. The siloxane block polymer may contain more than one siloxane block. For example, the siloxane block polymer may comprise a polydimethylsiloxane block and a polymethylphenylsiloxane block, or a polydivinylsiloxane block and a polydimethylsiloxane block.

The siloxane block may be for example, a polyalkyl siloxane, polyaryl siloxane, polyalkylaryl siloxanes, polyether siloxane copolymers and mixtures thereof.

$R_1$ and $R_2$ may be the same or different and are independently alkyl, alkoxy, aryl, aryloxy, alkylaryl, alkylamine, alkylhydroxy, polyoxyalkylene, and polyalkylene polyamine Alkyl is defined as linear or branched $C_1$-$C_{20}$. For example, alkyl may be $C_1$-$C_4$, $C_1$-$C_8$, $C_1$-$C_{12}$ or $C_1$-$C_{14}$.

$C_1$-$C_{20}$ alkyl is straight-chain or branched alkyl radicals, such as methyl, ethyl, n-propyl, iso-propyl, n-butyl, sec-butyl, tert-butyl, amyl, isoamyl or tent-amyl, heptyl, octyl, isooctyl, nonyl, decyl, undecyl, dodecyl, tetradecyl, pentadecyl, hexadecyl, heptadecyl, octadecyl or eicosyl.

For example, the siloxane block may be polydimethyl siloxane or polydiethylsiloxane. Polydimethylsiloxane is also known as dimethicone.

Methyl, ethyl and propyl or mixtures thereof are especially suitable as $R_1$ and $R_2$.

Aryl may be phenyl or alkyl substituted phenyl.

Arylated silicones are known to enhance shine characteristics of hair having a refractive indices of about 1.46 or higher, especially about 1.52 or higher.

Polymethylphenylsiloxane is an example of an arylated siloxane.

Alkylaryl may be for example, methyl, ethyl, t-butyl substituted phenyl.

Polyoxyalkylene is for example, polypropylene oxide and/or polyethylene oxide. The polyoxyalkylene may modify a polydialkylsiloxane. Alternatively, mixtures of alkylene oxides may be used to modify the base polysiloxane. For example polypropylene or polyethylene oxide may be used to modify polydimethylsiloxane. These materials are generally known as dimethicone copolyols. Thus the polysiloxane block may comprise dimethicone copolyols.

Alkoxy may be $C_1$-$C_4$ branched or linear alkoxy such as methoxy, ethoxy, propoxy and n-butoxy and t-butoxy.

Aryloxy may be for example, phenoxy or alkyl substituted phenoxy.

Alkylamines are for example, $C_1$-$C_4$ branched or linear alkyl radicals substituted by amines. The one or more amine substitution of the alkyl chain may occur anywhere on the chain such as at the end.

Alkylhydroxy $C_1$-$C_4$ branched or linear alkyl radicals substituted by hydroxy. The one or more hydroxy substitution of the alkyl chain may occur anywhere on the chain such as at the end.

Polyalkylenepolyamines are alkylene chains interrupted by amines.

For example, formula (IV) is representative of polyalkylenepolyamine substitution on a siloxane.

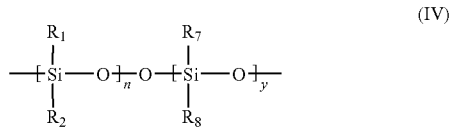

(IV)

The $R_1$, $R_2$ and n are defined as above and $R_7$ may be hydroxyl, $C_1$-$C_4$ alkoxy or $C_1$-$C_4$ alkyl, $R_9$ is —$(CH_2)_{1-4}$—$NR_9$—$(CH_2)_{1-4}$—$NR_9R_{10}$ and y is an integer from 1 to 10,000. $R_9$ and $R_{10}$ is the same or different and is hydrogen or $C_1$-$C_4$ alkyl.

The siloxane block of the amphiphilic block copolymer may for example be formula (IV).

When $R_1$ and $R_2$ are methyl, the above polymer (IV) is sometimes referred to as "amodimethicone".

References disclosing suitable siloxanes include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston, all of which are incorporated herein by reference in their entirety. Also incorporated herein by reference in its entirety is "Silicon Compounds" distributed by Petrarch Systems, Inc., 1984. This reference provides an extensive, though not exclusive, listing of suitable silicones.

The number of repeat units in the siloxane block will vary from about 2 to about 10,000, for example, from about 10 to 5000 and about 20 to about 1000.

The Cationic Block

The cationic block must be formed, at least partially, from at least diallydialkylammonium derived monomers.

For example, specific monomers of the diallydialkylammonium type are diallyldimethylammonium chloride (DADMAC), diallyldiethylammonium chloride, diallyldimethylammonium bromide, diallyldimethylammonium sulfate, diallydimethylammonium phosphate, diallyldi(beta-ethoxyethyl)ammonium chloride and diallyldi(beta-hydroxyethyl) ammonium chloride. The most preferred cationic monomer is DADMAC.

The counterion of $Y^-$ may be virtually any counterion. $Y^-$ may be a counterion, represented by but not limited to chloride, bromide, iodide, substituted or unsubstituted aryl sulfonates, sulfate, alkyl sulfonates such as methyl sulfonate, ethyl sulfonate, carboxylates, nitrate, phosphates, tetrafluoroborate, tetraalkylborate, tetraarylborate, perchlorate, and hexafluorophosphate.

The number of repeat units in the cationic block ranges from about 2 to 5000. For example, the repeat units may range from about 2 to about 1000 or from about 10 to about 500.

The hydrophilic or cationic polymer block may be a homopolymer or random copolymer, block copolymer or a grafted polymer or copolymer.

The cationic polymer blocks may be any molecular weight. The preferred average molecular weight however will vary from about 500 g/mole to about 1,000,000 g/mole, about 500 g/mole to about 500,000 g/mole, about 800 g/mole to about 500,000 g/mole and more preferably from about 800 g/mole to 100,000 g/mole, for example, about 800 g/mole to about 10,000 g/mole or about 1,000 g/mole to about 5,000 g/mole.

The diallyldialkylammonium polymer block may be separately synthesized by any suitable polymerization process. The diallydialkylammonium polymers may be prepared for instance as gel polymers by solution polymerization, water-in-oil suspension polymerization or by water-in-oil emulsion polymerization. When preparing gel polymers by solution polymerization the initiators are generally introduced into the monomer solution.

The diallyldialkylammonium polymer block may be produced separately as beads by suspension polymerization or as a water-in-oil emulsion or dispersion by water-in oil emulsion polymerization, for example according to a process defined by EP150933, EP-102760 or EP-126528.

The diallyldialkylammonium block may be synthesized by conventional radical polymerization or by controlled polymerizations.

The blocks may be formed first, then covalently linked to form the final block copolymer.

Other ethylenically unsaturated monomers in addition to the diallydialkylammonium monomer may be used to form the cationic block of the amphiphilic block copolymer.

For example nonionic, anionic or cationic monomers may be included in the cationic block containing diallydialkylammonium repeat units.

Specific nonionic monomers for example are (meth)acrylamide, 2-hydroxyethyl acrylate, (meth)acrylate esters and N-vinylpyrrolidone. (Meth) acrylate esters for example are methyl (meth)acrylate and ethyl (meth)acrylate.

Additional cationic monomers may be selected from acid addition salts or quaternary ammonium salts of either dialkyl amino alkyl (meth)acrylate or dialkyl amino alkyl (meth) acrylamides.

Representative examples are cationically charged or potentially cationically charged monomers including dimethylaminoethyl acrylate methyl chloride quaternary salt, dimethylaminoethyl acrylate methyl sulfate quaternary salt, dimethyaminoethyl acrylate benzyl chloride quaternary salt, dimethylaminoethyl acrylate sulfuric acid salt, dimethylaminoethyl acrylate hydrochloric acid salt, dimethylaminoethyl methacrylate methyl chloride quaternary salt, dimethylaminoethyl methacrylate methyl sulfate quaternary salt, dimethylaminoethyl methacrylate benzyl chloride quaternary salt, dimethylaminoethyl methacrylate sulfuric acid salt, dimethylaminoethyl methacrylate hydrochloric acid salt, diethylaminoethyl acrylate, diethylaminoethyl acrylate methyl chloride quaternary salt, diethylaminoethyl methacrylate, diethylaminoethyl methacrylate methyl chloride quaternary salt, methacrylamidopropyltrimethylammonium chloride, acrylamidopropyltrimethylammonium chloride, dimethylaminopropylacrylamide methyl sulfate quaternary salt, dimethylaminopropylacrylamide sulfuric acid salt or dimethylaminopropylacrylamide hydrochloric acid salt.

Typically the anionic monomer may be any ethylenically unsaturated carboxylic acid or sulphonic acid. For example, anionic monomers may be (meth)acrylic acid or 2-acrylamido-2-methylpropane sulphonic acid.

The cationic block polymer may be random, structured, or comprised of various blocks. The cationic block for example might be a random or block copolymer of DADMAC and an ammonium salt of dimethylaminoethyl (meth)acrylate, a homopolymer block of DADMAC, a random or block copolymer of DADMAC and acrylamide or a random or block copolymer of DADMAC and acrylic acid.

The Formed Amphiphilic Block Copolymer

It is preferable that the formed block amphiphilic copolymer is neither irritating, toxic nor otherwise harmful when applied to the hair, and is compatible with the other components of the composition, is chemically stable under normal use and storage conditions, and is capable of being deposited on and conditions the keratinous substrate.

It is also preferable that the formed block amphiphilic copolymer is water soluble or water dispersible.

The weight ratio of the siloxane block to cationic block will vary. The weight ratio for siloxane:cationic may vary from about 1:100 to about 100:1, for example about 1:10 to about 10:1 based on the total weight of the formed amphiphilic block copolymer. Additional, weight ratios envisioned may be about 1:4 to about 4:1, about 1:3 to about 3:1, about 1:2 to about 2:1 or about 1:1.

The total molecular weight of the formed amphiphilic block copolymer will vary widely depending upon the application.

The repeat unit molar ratio of siloxane units to cationic units may vary widely. For example, about 1:100 to about 100:1, about 1:25 to about 25:1, about 1:10 to about 10:1 are envisioned of about 1:3 to about 3:1. by way of example, if the amphiphilic block copolymer has an excess of cationic repeat units, for example 1 siloxane repeat units to every cationic unit, the ratio would be about 1:2 or 5.

An excess of cationic units may be preferable.

These amphiphilic block copolymers of the invention are particularly useful for cleansing, treating, or protecting keratinous substrates.

As mentioned above, the amphiphilic block copolymers of the invention may be combined with a detersive surfactant in conditioning shampoos. Such conditioning shampoos include 2 and 1 shampoos which incorporate a conditioning agent which deposits onto the hair and remains on the hair after washing is complete.

The incorporation of amphiphilic block copolymer in shampoos has been found to be beneficial both as a conditioning agent by itself and as a deposition aid for delivering additional conditioning agents to hair.

Conditioning agents for hair are, for example, agents such as silicones, polydiorganosiloxanes such as polydimethylsiloxanes, hydroxyl functional silicones and amino functional silicones. These silicones may be used at amounts that vary anywhere from about 0.01 wt. % to 5.0 wt. %, preferably amounts vary from about 0.01 to about 3.0 wt. %.

The additional conditioning agents such as the silicones described above (different than the conditioning amphiphilic block copolymer of the invention) may be combined with the block copolymer of the invention.

The amphiphilic block copolymer of the invention will typically be combined with a detersive surfactant when used in a shampoo. One of the chief advantages of the amphiphilic block copolymer of the invention is its compatibility with multiple surfactants.

By compatibility, it is meant that stable solutions may be formed using the inventive amphiphilic copolymer.

The amphiphilic block copolymer of the invention may for example be added to a hair conditioning shampoo compositions at amounts that range from about 0.01 to about 5.0 wt. % based on the total composition. More preferable amounts may range from about 0.01 to about 2.5 or 0.01 to about 1.0 wt. %.

Preparation of the Amphiphilic Block Copolymer

The Amphiphilic Block copolymer may be formed by polymerizing a diallydialkylammonium monomer in the presence of a suitably terminated polysiloxane.

Suitably terminated with a chain transfer group for purposes of the invention means termination or pendant termination with a thiol, xanthate, dithioester, trithioester, dithiocarbamate, secondary alcohol or nitroxyl. For example U.S. Pat. No. 6,858,696 discloses polysiloxanes derivatized with a xanthate herein incorporated entirely by reference.

A thiol terminated hydrophobic block may be synthesized by treating for example, polysiloxane resin having terminal double bonds or hydroxyl groups with such reagents as thioacetic acid, thiobenzoic acid, thiopropionic acid, thiobutyric acid, thiovaleric acid or secondary alcohol. The synthesis is described for example in Japanese Application No. 09031145 (1995) and Ying Jun Du et al. in *J. Applied Polymer. Sci.*, 2003, 594.

Polysiloxanes of various average molecular weights which are terminated with double bonds or hydroxyl groups are available commercially. For example, Siltech Coporation supplies a range of reactive polysiloxanes under the tradenames SILMER OH and SILMER VIN.

The block copolymer may then be directly formed by polymerizing the cationically charged diallydialkylammonium monomer in the presence an initiator and the suitably terminated polysiloxane block.

It is also possible that the polysiloxane block be grafted with pendant chain transfer groups such as thiols. The cationic monomer, for example DADMAC, would then be polymerized in the presence of a polysiloxane polymer with thiol pendant groups, giving a grafted block copolymer with grafted cationic blocks.

The polymerization initiator can be any initiator such as those activated by heat, light or electromagnetic radiation or an oxidizing or reducing agent.

Typical initiators are for example, azobis compounds such as azobisisobutyronitrile, azobis-2,4-dimethylvaleronitrile, azobiscyclohexane carbonitrile, azobis-2-amidinopropane hydrochloride, dimethyl azobisisobutyrate, azobisisobutylamidine hydrochloride and 4,4'-azobis-4-cyanovaleric acid, peroxide initiators such as benzoyl peroxide, benzoyl 2,4-dichloroperoxide, di-tert-butyl peroxide, lauroyl peroxide, acetyl peroxide, diisopropyl dicarbonate peroxide, cumene hydroperoxide, tert-butyl hydroperoxide, dicumyl peroxide, p-menthane hydroperoxide, pinane hydroperoxide, methyl ethyl ketone peroxide, cyclohexanone peroxide, diisopropyl peroxy dicarbonate, tert-butyl peroxy laurate, di-tert-butyl peroxy phthalate, dibenzyl oxide and 2,5-dimethylhexane-2, 5-dihydroperoxide, and redox initiators such as benzoyl peroxide-N,N-dimethyl aniline, peroxodisulfuric acid-sodium hydrogen sulfite and salts of persulfate such as sodium, potassium or ammonium persulfate.

Photoinitiators are also envisioned.

The reaction solvent includes, for example, aliphatic hydrocarbons such as pentane, hexane, heptane, octane, decane, dodecane and tetradecane, alicyclic hydrocarbons such as cyclopentane, methylcyclopentane, cyclohexane, methylcyclohexane, cyclooctane and cyclohexene, aromatic hydrocarbons such as benzene, toluene and xylene, halogenated hydrocarbons such as dichloromethane, chloroform, dichloroethane, dichloropropane, trichloroethylene, chlorobenzene, dichlorobenzene and 2,4-dichlorotoluene, esters such as methyl acetate, ethyl acetate and butyl acetate, ketones such as acetone and methyl ethyl ketone, and dioxane, tetrahydrofuran, acetonitrile, dimethylformamide, dimethyl sulfoxide and alcohols such as methanol, ethanol, propanol, isopropanol, n-butanol, isobutanol, sec-butanol, and t-butanol.

The addition of surfactants to the solvents is also envisioned.

These can be used alone or as a mixture thereof. Mixtures of solvents may be preferable.

Detersive Surfactants

Detersive surfactants may be anionic, nonionic, amphoteric or zwitterionic surfactants, or mixtures thereof. The purpose of the detersive surfactant is to provide cleansing performance to the shampoo composition. The term detersive surfactant, as used herein, is intended to distinguish these surfactants from surfactants which are primarily emulsifying surfactants, i.e. surfactants which provide an emulsifying benefit and which have low cleansing performance. It is recognized that most surfactants have both detersive and emulsifying properties. It is not intended to exclude emulsifying surfactants from the present invention, provided the surfactant also possesses sufficient detersive properties to be useful herein.

The detersive surfactants will generally comprise from about 5% to about 50%, for example, about 8% to about 30% or about 10 to about 25% by weight of the shampoo composition.

Anionic Surfactants

Suitable anionic detersive surfactant components for use in the shampoo composition herein include those which are known for use in hair care or other personal care cleansing compositions. The concentration of the anionic surfactant component in the shampoo composition should be sufficient to provide the desired cleaning and lather performance, and generally range from about 5% to about 50%, preferably from about 8% to about 30%, more preferably from about 10% to about 25%, even more preferably from about 12% to about 22%, and most preferably from about 7 to about 20% by weight of the composition.

Anionic surfactants suitable for use in the shampoo compositions are the alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Solubility of the surfactant will depend upon the particular anionic detersive surfactants and cations chosen.

R may be from about 8 to about 18 carbon atoms, for example, from about 10 to about 16 carbon atoms, even from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 1 to about 5, more preferably about 2 to 3, molar proportions of ethylene oxide, and the resulting mixture of molecular species having, for example, an average of 3 moles of ethylene oxide per mole of alcohol, is sulfated and neutralized.

Specific non-limiting examples of alkyl ether sulfates which may be used in the shampoo compositions of the present invention include sodium and ammonium salts of coconut alkyl triethylene glycol ether sulfate, tallow alkyl triethylene glycol ether sulfate, tallow alkyl hexa-oxyethylene sulfate, and alkyldiethylene glycol ether sulfate. Typical alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic detersive surfactants are the water-soluble salts of organic, sulfuric acid reaction products conforming to the formula $[R_1—SO_3\text{-}M]$ where $R_1$ is a straight or branched chain, saturated, aliphatic hydrocarbon radical having from about 8 to about 24, for example, about 10 to about 18, carbon atoms; and M is a cation described hereinbefore. Non limiting examples of such detersive surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278, which descriptions are incorporated herein by reference.

Other anionic detersive surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880, which description is incorporated herein by reference.

Another class of anionic detersive surfactants suitable for use in the shampoo compositions are the beta-alkyloxy alkane sulfonates. These surfactants conform to the formula

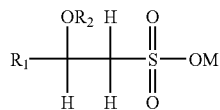

where $R_1$ is a straight chain alkyl group having from about 6 to about 20 carbon atoms, $R_2$ is a lower alkyl group having from about 1 to about 3 carbon atoms, preferably 1 carbon atom, and M is a water-soluble cation as described hereinbefore.

Yet another class of anionic detersive surfactants suitable for use in the shampoo compositions are alkyl glyceryl ether sulfonate surfactants (also referred to herein as an "AGS" surfactant), derivatives thereof and salts thereof. AGS surfactants are derived from an alkyl glyceryl ether containing a sulfonate or sulfonate salt group. These compounds generally can be described as an alkyl monoether of glycerol that also contains a sulfonate group.

These AGS surfactants can be described as generally conforming to the following structures:

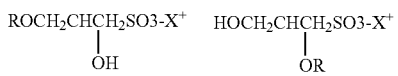

wherein R is a saturated or unsaturated straight chain, branched chain, or cyclic alkyl group having from about 10 to about 18 carbon atoms, preferably from about 11 to about 16 carbon atoms, and most preferably from about 12 to about 14 carbon atoms, and X is a cation selected from the group consisting of ammonium; mono-alkylsubstituted ammonium; di-alkylsubstituted ammonium; tri-alkylsubstituted ammonium; tetra-alkylsubstituted ammonium; alkali metal; alkaline metal; and mixtures thereof. More preferably, the alkyl radicals, R in the above formulas, are saturated and straight chain.

Anionic detersive surfactants for use in the shampoo compositions may include ammonium lauryl sulfate, ammonium lauryl ether sulfate (varying degrees of ethoxylation), ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Some of the most commonly used detersive surfactants are sodium lauryl sulfate, sodium laureth-1 sulfate (lauryl with 1 mole of ethylene oxide), sodium laureth-2-sulfate (lauryl with 2 moes of ethylene oxide), sodium laureth-2-sulfate (lauryl with 3 moles of ethylene oxide), and the corresponding ammonium salts.

Suitable amphoteric or zwitterionic detersive surfactants for use in the shampoo composition herein include those which are known for use in hair care or other personal care cleansing. Concentration of such amphoteric detersive surfactants preferably ranges from about 0.5% to about 20%, preferably from about 1% to about 10%, by weight of the composition. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.), which descriptions are incorporated herein by reference.

Amphoteric Surfactants

Amphoteric detersive surfactants suitable for use in the shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Amphoteric detersive surfactants for use in the present invention for example, include cocoamphoacetate, cocoamphodiacetate, lauroamphoacetate, lauroamphodiacetate, alkylaminoalkanoic acids, alkylaminoalkanoates and mixtures thereof. An example of alkylaminoalkanoates is cocaminopropionic acid.

Zwitterionic Surfactants

Zwitterionic detersive surfactants suitable for use in the shampoo composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred. A particularly preferred betaine is cocamidopropyl betaine.

The shampoo compositions of the present invention may further comprise additional surfactants for use in combination with the anionic detersive surfactant component described hereinbefore. Suitable optional surfactants include nonionic surfactants and cationic surfactants. Any such surfactant known in the art for use in hair or personal care products may be used, provided that the optional additional surfactant is also chemically and physically compatible with the essential components of the shampoo composition, or does not otherwise unduly impair product performance, aesthetics or stability. The concentration of the optional additional surfactants in the shampoo composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the shampoo compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which descriptions are incorporated herein by reference.

Polyalkylene Oxide Alkyl Ether

The composition of the present invention may include one or more polyalkylene oxide alkyl ethers. Polyalkylene oxide alkyl ether is a polyethylene glycol alkyl ether, a polypropylene glycol alkyl ether, polyethylene glycol polypropylene glycol alkyl ethers, and combinations thereof.

Specific examples of useful polyalkylene oxide alkyl ethers include PPG-15 stearyl ether (available as ARLAMOL E from Uniqema), polyoxypropylene (9) decyl ether, polyoxypropylene (4) polyoxyethylene (6) cetyl ether, and polyoxyethylene (12) behenyl ether.

The compositions of the present invention may include an aqueous carrier. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, for example ethanol and isopropanol.

The aqueous carrier is typically substantially water. Deionized water is preferably used. Water from natural sources containing mineral cations can also be used, depending on the desired characteristic of the product. Generally, the compositions of the present invention comprise from about 20% to about 95%, preferably from about 40% to about 92%, and more preferably from about 60% to abut 90% aqueous carrier.

The pH of the present composition is preferably from about 4 to about 9, more preferably from about 4.5 to about 7.5. Buffers and other pH adjusting agents can be included to achieve the desirable pH.

Additional Components

The shampoo compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the shampoo composition.

Non-limiting examples of optional components for use in the shampoo composition include cationic polymers such as cationic starches (in addition to the inventive amphilphilic block copolymer), particles, conditioning agents (hydrocarbon oils, fatty esters, silicones), anti dandruff agents, suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

Starches are optional components for use in shampoos and skin formulations. The starches may be derived from virtually any source such as cereals, tubers, roots, legumes and fruits. The native source can be corn, pea, potato, sweet potato, banana, brley, wheat, rice, sago, amaranth, taioca, arrowroot, canna, sorghum and waxy. The sources include high amylose or high amylopectin varieties thereof. High amylopectin varieties means for purposes of the invention containing at least about 60 wt. % amylopectin or at least about 70 wt. % amylopectin. High amylase includes greater than about 40 weight % amylose. For example, potato starch normally contains about 80% amylopectin and about 20% amylase. Thus potato starch would be a high amylopectin variety of starch.

The starches include derivative such as anionic, cationic or nonionic derivatives.

The nonionic starch derivatives may be derivatized for example by using alkylene oxides.

Anionic modification of starches may be accomplished by any reagent known in the art, such as alkenyl succinic anhydrides, inorganic phosphates, sulfates, phosphonates, sulfonates and sodium chloroacetic acids.

Cationic modification may be accomplished by any reagent known in the art including those reagents containing amino, imino, ammonium, sulfonium, or phosphonium groups. Such cationic derivatives include those with nitrogen containing groups comprising primary, secondary, tertiary and quaternary amines and sulfonium and phosphonium groups attached through either ether or ester linkages. Cationic modification, particularly tertiary amino or quaternary ammonium etherification is typically prepared by treatment with 3-chloro,-2-hydroxylpropyltrimethylammonium chloride or the like.

The cationic degree of substitution on the starch may vary widely from about 0.1 to about 4.

The starch may be hydrolyzed to reduce the molecular weight by any method known in the art such as oxidation or enzyme hydrolysis. The starch may also be undegraded and even further crosslinked to increase the molecular weight.

The starch may be used in hair conditioning formulations in amounts that range from about 0.1 to about 5 weight % of the total formulation.

Method of Manufacture

The shampoo compositions of the present invention can be prepared by using various formulation and mixing techniques or methods known in the art for preparing surfactant or conditioning compositions, or other similar compositions.

Method of Use

The shampoo compositions of the present invention are used in a conventional manner for cleansing and conditioning hair or skin. An effective amount of the composition for cleansing and conditioning the hair or skin is applied to the hair or skin, that has preferably been wetted with water, and then rinsed off. Such effective amounts generally range from about 1 g to about 50 g, preferably from about 1 g to about 20 g. Application to the hair typically includes working the composition through the hair such that most or all of the hair is contacted with the composition.

This method for cleansing and conditioning the hair comprises the steps of: a) wetting the hair with water, b) applying an effective amount of the shampoo composition to the hair, and c) rinsing the shampoo composition from the hair using water. These steps can be repeated as many times as desired to achieve the desired cleansing and conditioning benefit.

The amphiphilic block copolymer of the invention is useful not only as a conditioning agent for skin and hair but is also useful as a deposition aid for other conditioning agents.

EXAMPLES

The examples illustrate specific embodiments of the present invention, but are not intended to be limiting thereof. Other modifications can be undertaken by the skilled artisan without departing from the spirit and scope of this invention.

All exemplified shampoo compositions can be prepared by conventional formulation and mixing techniques. Component amounts are listed as weight percents and exclude minor materials such as diluents, filler, and so forth. The listed formulations, therefore, comprise the listed components and any minor materials associated with such components.

Synthesis of Thiol Terminated Polysiloxanes

Example 1

Conversion of Vinyl End-Functional Polysiloxane into Thiol 20 g vinyl end-functional polydimethylsiloxane (Silmer VIN 100, Siltech) is dissolved in 20 mL toluene. To this is added 550 mg azobisisobutyronitrile and 0.8 mL thioacetic acid. The mixture is sparged with nitrogen for 30 min, then heated at 80° C. for 6 h. It is cooled in ice/water and rinsed with methanol three times. The residual solvent is removed under vacuum.

15 g of the product is dissolved in 20 mL toluene, and 2 mL 10% methanolic sodium hydroxide is added. The mixture is sparged with nitrogen and stirred for 8 h. It is rinsed with methanol 3 times. The residual solvent is removed under vacuum.

Example 2

To a solution of 25 g vinyl end-functional polydimethylsiloxane (Silmer VIN 200, Siltech) in 20 mL toluene is added 413 mg azobisisobutyronitrile and 0.6 mL thioacetic acid. The mixture is sparged with nitrogen for 30 min, then heated at 80° C. for 7 h. It is allowed to cool and rinsed with methanol three times. The residual solvent is removed under vacuum. To a solution of 2.0 g of this product in 2 ml ether that had been kept on lithium aluminum hydride (LAH) is added 50 mg LAH, and the mixture is stirred at room temperature for 48 h. The mixture is then filtered, and the solvent is removed under vacuum.

Example 3

Conversion of Hydroxyl End-Functional Polydimethylsiloxane into Thiol 20 g hydroxyl end-functional polydimethylsiloxane (Silmer OH100, Siltech) is dissolved in 50 mL dichloromethane. To this is added 2 mL pyridine and 4.0 g p-toluenesulfonyl chloride. The mixture is stirred at room temperature for 24 h. The product is rinsed with methanol 3 times, and the residual solvent is removed under vacuum. 5 g of the product is dissolved in 15 mL toluene and a solution of 0.45 g potassium thioacetate in 1.5 mL methanol is added. The mixture is sparged with nitrogen for 30 min., then stirred at 105° C. for 24 h. The mixture is allowed to cool, then rinsed with methanol 3 times, and the residual solvent is removed under vacuum. The product is dissolved in 10 mL toluene, and 1 mL 10% methanolic potassium hydroxide is added. The mixture is sparged for 30 min, then refluxed for 1 h. It is cooled in an ice bath, then rinsed with methanol 3 times, and the residual solvent is removed under vacuum.

Example 4

Synthesis of Block Copolymers of Polydimethylsiloxane and Diallyldimethylammonium Chloride (DADMAC)

A polymerization flask is charged with 4.0 g of the thiol end-functional polydimethylsiloxane of Example 1, 6.0 g dry DADMAC, 20 mL n-butanol, and 164 mg 2,2'-azobis(2-amidinopropane) dihydrochloride. After the DADMAC had dissolved, the mixture is sparged with nitrogen for 30 min, then heated and stirred at 70° C. for 24 h. It is allowed to cool. The product is precipitated with acetone and filtered. The white solid is dried in vacuum overnight. The product is stirred in 100 mL THF for 1 h, then filtered, rinsed with THF and dried in vacuum.

Several additional amphiphilic triblock copolymer of polysiloxane and DADMAC are synthesized varying the average molecular weight of the starting polysiloxane and source polydimethylsiloxane (OH or vinyl terminated). Triblock copolymers of polydimethylsiloxane and polyDADMAC were formed as shown below in Table I.

TABLE 1

Triblock Copolymers of Polysiloxane and PolyDADMAC

| Example | Polysiloxane[1] | $M_n$ (silicone)[2] | Si/DADMAC Molar ratio of repeating units |
|---|---|---|---|
| 5 | OH Terminated Polysiloxane | 7700 | 0.61 |
| 6 | OH Terminated Polysiloxane | 7700 | 0.78 |
| 7 | OH Terminated Polysiloxane | 7700 | 0.52 |
| 8 | OH Terminated Polysiloxane | 7700 | 0.45 |
| 9 | Vinyl terminated Polysiloxane | 6000 | 0.5 |
| 10 | Vinyl terminated Polysiloxane | 6000 | 0.6 |
| 11 | Vinyl terminated Polysiloxane | 6000 | 0.59 |
| 12 | Vinyl terminated Polysiloxane | 6000 | 0.84 |
| 13 | Vinyl terminated Polysiloxane | 6000 | 0.80 |
| 14 | Vinyl terminated Polysiloxane | 10,800 | 0.44 |
| 15 | Vinyl terminated Polysiloxane | 10,800 | 0.56 |
| 16 | Vinyl terminated Polysiloxane | 10,800 | 0.69 |

[1]The functional polysiloxanes are purchased from Siltech Corporation. The $M_n$ is the starting material $M_n$.

The amphiphilic block copolymers (triblock polyDADMAC-polydimethylsiloxane-polyDADMAC) are tested on hair in 2 in 1 shampoo formulations.

2 in 1 Shampoo Formulations

Table II gives the formulation of the 2 and 1 shampoo. The inventive amphiphilic block copolymers are added to the formulation below at 0.05 and 0.1 weight percent concentration. The formulations below incorporating the amphiphilic block copolymers are compared to control shampoo formulations wherein the amphiphilic block copolymer is replaced with a cationic polymer at 0.05 and 0.1 weight % (cationic cellulose, Polyquaternium 10 or Guar hydroxypropyl trimethylammonium chloride) and 2 weight % polydimethylsiloxane.

TABLE II

| Component | Weight % |
|---|---|
| Water (QS to 100%) | |
| ALES-3[1] | 10 |
| ALS[2] | 4 |
| Cocamidopropyl Betaine | 3 |
| Ethylene Glycol distearate | 2 |
| Cetyl Alcohol | 1.5 |
| Cocamide MEA | 1.0 |
| Amphiphilic Block Copolymer (examples 5-8) | 0.10 and 0.05 |

[1]Ammonium lauryl ether (3 ethoxylate units) sulfate.
[2]Ammonium lauryl sulfate.

The shampoo pH is adjusted to 5.5. Sodium chloride is used to adjust the viscosity of the shampoos to approximately 6000 cps. The control formulations with polysiloxane and Polyquaternium 10 or Guar hydroxypropyl trimethylammonium chloride polyquaternium 10 are homogenized until a polysiloxane droplet size ranging from 0.1 to about 20.0 microns are attained.

Table III shows the measured values of hair treated with the amphiphilic block copolymers and the results for substantivity and build-up of silicone, and reductions in wet and dry combing energies on hair.

Examples 17 and 18 are formulated in the 2 and 1 shampoo as in Table II except the block copolymers are added at 0.5 wt. %. Comparison are made using the amphiphilic block copolymer alone and in combination with a cationic potato starch.

TABLE III

PolyDADMAC-Siloxane-PolyDADMAC Block Copolymer Conditioning Properties

| Sample | Cationic Polymer | Wt. % of Formulation (wt. %) | Substantivity (μg/g hair)[1] | Build-Up (μg/g hair) | Red. in Wet Comb energy (%)[5] | Red. in dry Comb energy (%)[5] | Ability to deliver silicone to hair (μg/g hair)[2] | Hair Vol. %[3] | Compatibility with surfactant[4] |
|---|---|---|---|---|---|---|---|---|---|
| Control | PQ-10 | 0.1 | 0.411 | 0.051 | 47.1 | 42.1 | 107.9 | 100 | Clear Stable |
|  |  | 0.05 | 0.237 | 0.022 | 26.7 | 15.4 |  |  |  |
| Control | Cationic Guar Gum | 0.1 | 0.453 | 0.073 | 53.3 | 45.4 | 123.6 | −12 | Clear Stable |
|  |  | 0.05 | 0.332 | 0.043 | 35.4 | 24.7 |  |  |  |
| Example 5 |  | 0.1 | 0.047 | 0.005 | 45.6 | 56.7 | 46.3 | 64 | Hazy Unstable |
|  |  | 0.05 | 0.032 | 0.003 | 45.4 | 55.4 |  |  |  |
| Example 6 |  | 0.1 | 0.042 | 0.004 | 46.1 | 55.7 | 44.1 | 62 | Hazy Unstable |
|  |  | 0.05 | 0.038 | 0.003 | 44.8 | 56.8 |  |  |  |
| Example 7 |  | 0.1 | 0.048 | 0.004 | 46.7 | 57.6 | 45.4 | 66 | Slightly hazy Stable |
|  |  | 0.05 | 0.033 | 0.003 | 45.9 | 54.9 |  |  |  |
| Example 8 |  | 0.1 | 0.044 | 0.004 | 46.3 | 55.8 | 32.4 | 54 | Slightly hazy Stable |
|  |  | 0.05 | 0.023 | 0.003 | 45.3 | 55.2 |  |  |  |

[1]Build-up and substantivity evaluations are made by applying shampoo for recommended time and thoroughly rinsing the shampooed tresses. The tress is then immersed in dye solution (Pyrazol Bordeaux) for 5 minutes. Tresses are removed from the dye solution and rinsed until no more dye elutes. The tresses are then immersed in an isopropyl acohol/water (IPA/H2O) solution for 5 minutes and rinsed with tap water. The dye absorbance of the IPA/H2O solution is measured and the microgramsof dye per gram of hair is calculated via a calibration curve.
[2]Is determined by the same method described in 1 above. The amphiphilic block copolymers are formulated with an additional 2 wt. % polydimethylsiloxane.
[3]Volume index % values are measured using a DIA-STRON MTT175 tensile tester on 12 g tresses of hair. The pulling work for the untreated hair tresses is compared to the treated hair tresses. The difference between the two is the volume index %.
[4]Stability evaluation are made by placing the formulated shampoos in an oven at 40° C. for 1 month and noting the stability and clarity of the formulated shampoos.
[5]Combing analysis for wet and dry tresses are made using a MINI-TENSILE TESTER DIA-STRON. As in all other tests, the tresses are 8 inches long brown European virgin untreated hair. The wet combing measurements are determined after the hair tresses are washed, first, with a control shampoo and, then, with the shampoos containing the polymers for evaluation. The method consists in applying 1 g of the shampoo under consideration to a 5 g gram wet hair tress, then, rubbing gently withthe fingers for 1 minute while foam is produced. Subsequently, the hair tresses are rinsed for 30 seconds with luke warm water. The excess water is squeezed with the fingers and the hair tresses are placed in a Mini-Tensile Tester. The difference in combining energies between the untreated and treated wet samples are measured and compared. Measurements are done in triplicate. The combing analyses for the dry tresses are carried out in the same way except that the hair tresses are driedbefore measurement.

Synthesis of Block Copolymers of Polydimethylsiloxane and Diallyldimethylammonium/Dimethylaminoethylmethacrylate Example 17

A 1000 ml flask is charged with 50 g of thiol end-functional polydimethylsiloxane (MW ~6000). To this is added a dispersion of 50 g of dried diallyldimethylammonium chloride in 200 ml of n-butanol, 50 g of dimethylaminoethyl methacrylate, 175 ml of n-butanol, and 2.5 g 2,2'-azobis(2-amindinopropane)dihydrochloride. The mixture is sparged with nitrogen for 1 hr, then stirred at 80 C for 6.5 hrs, after which the temperature is raised to 100 C for 30 minutes. The solvent is removed under vacuum.

Example 18

Example 18 is identical to example 17 above except that 25 g of diallyldimethylammonium chloride and 75 g of dimethylaminoethyl methacrylate are used.

Table IV

Shows the measured reduction in wet combing energy values of hair treated with an amphiphilic block Reduction in 2 and 1 Formulations.

The tests in Table IV are carried out using the same methodology as described in Table III.

| Sample | Cationic Polymer | Cationic Starch (wt. %) | Red. in Wet Comb energy (%) |
|---|---|---|---|
| 19 |  | 0.5 | 63.5 |
| 20 | Example 17 |  | 46.3 |
| 21 | Example 18 |  | 44.8 |
| 22 | Example 17 | 0.5 | 76.65 |
| 23 | Example 18 | 0.5 | 77.7 |

Summary of Results

The amphiphilic block copolymers:
   show good dry conditioning and moderate wet conditioning properties at substantially lower active concentrations (0.05 wt. %) than those concentrations which use commercial cationic conditioning polymers (PQ-10 or Cationic Guar Gum) and 2% polydimethylsiloxane;

show low substantivity and buildup;
show good wet and dry combing force reduction at very low concentrations;
are able to deliver moderate amounts of silicone to hair when used in combination with a polysiloxane conditioning agent;
show a moderate volumizing effect; and
form stable formulations.
show synergism when combined with cationic starch.

We claim:

1. A hair conditioning shampoo composition comprising:
a) a linear amphiphilic block copolymer comprising at least siloxane polymer block of formula (I)

wherein n is a number between 2 and 10,000,
and
a cationic polymer block formed from at least a cationic monomer of formula (II)

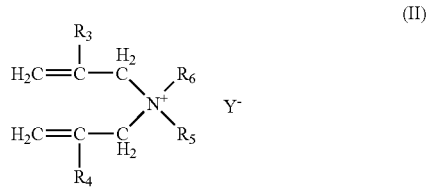

wherein $R_3$ and $R_4$ are independently of one another hydrogen or $C_1$-$C_4$ alkyl; $R_5$ and $R_6$ are, independently, hydrogen or an alkyl, hydroxyalkyl, carboxyalkyl, carboxyamidalkyl or alkoxyalkyl groups having from 1 to 18 carbon atoms; and $Y^-$ represents an anion,
and
b) an anionic detersive surfactant.

2. The hair conditioning shampoo according to claim 1, wherein the siloxane polymer block is a polymer of formula (I)

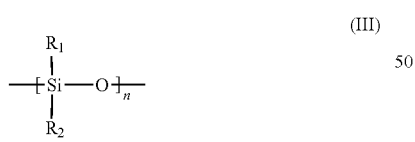

wherein $R_1$ and $R_2$ are independently alkyl, alkoxy, phenylalkyl, aryl, aryloxy, alkylaryl, alkylamine, alkylhydroxy, polyoxyalkylene and polyalkylene polyamine, n is a number between 2 to 10,000.

3. The hair conditioning shampoo composition according to claim 1, wherein the cationic monomer of formula II is selected form the group of monomers consisting of diallyldimethylammonium chloride (DADMAC), diallyldiethylammonium chloride, diallyldimethylammonium bromide, diallyldimethylammonium sulfate, diallydimethylammonium phosphate, diallyldi(beta-ethoxyethyl)ammonium chloride and diallyldi(beta-hydroxyethyl)ammonium chloride.

4. The hair conditioning shampoo composition according to claim 1, wherein the cationic polymer block is formed from at least a cationic monomer of formula (II) and a second cationic monomer selected from the group consisting of ammonium or quaternary salts of dialkyl amino alkyl(meth)acrylates and dialkyl amino alkyl(meth)acrylamides.

5. The hair conditioning shampoo composition according to claim 4, wherein the second cationic monomer is dimethylaminoethyl acrylate methyl chloride quaternary salt, dimethylaminoethyl acrylate methyl sulfate quaternary salt, dimethyaminoethyl acrylate benzyl chloride quaternary salt, dimethylaminoethyl acrylate sulfuric acid salt, dimethylaminoethyl acrylate hydrochloric acid salt, dimethylaminoethyl methacrylate methyl chloride quaternary salt, dimethylaminoethyl methacrylate methyl sulfate quaternary salt, dimethylaminoethyl methacrylate benzyl chloride quaternary salt, dimethylaminoethyl methacrylate sulfuric acid salt, dimethylaminoethyl methacrylate hydrochloric acid salt, diethylaminoethyl acrylate, diethylaminoethyl acrylate methyl chloride quaternary salt, diethylaminoethyl methacrylate, diethylaminoethyl methacrylate methyl chloride quaternary salt, methacrylamidopropyltrimethylammonium chloride, acrylamidopropyltrimethylammonium chloride, dimethylaminopropylacrylamide methyl sulfate quaternary salt, dimethylaminopropylacrylamide sulfuric acid salt or dimethylaminopropylacrylamide hydrochloric acid salt.

6. The hair conditioning shampoo composition according to claim 1, wherein the amphiphilic block copolymer is a diblock or triblock amphiphilic block copolymer.

7. The hair conditioning shampoo composition according to claim 1, wherein the amphiphilic block copolymer is water soluble or water dispersible.

8. The hair conditioning shampoo composition according to claim 1, wherein the weight ratio of the siloxane polymer block to cationic polymer block varies from about 1:100 to about 100:1.

9. The hair conditioning shampoo composition according to claim 1, wherein the amphiphilic block copolymer is defined by the formula III

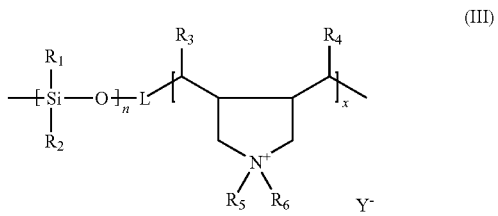

wherein $R_1$, $R_2$, $R_3$, $R_4$, R5, R6, n and $Y^-$ are as defined in claim 2 and x is an integer between 2 and 1000 and L is a linking group.

10. The hair conditioning shampoo composition according to claim 9, wherein the linking group contains sulfur.

11. The hair conditioning shampoo composition according to claim 9 wherein formula (III) is

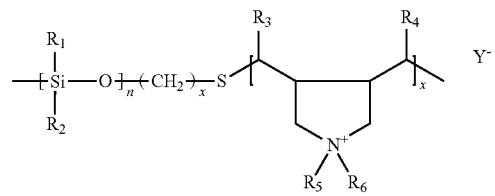

and x is 1-10.

12. The hair conditioning shampoo composition according to claim 1, further comprising a starch.

13. A hair conditioning shampoo composition according to claim 12, wherein the starch is cationic.

14. The compositions according to claim 1, wherein the anionic surfactant is selected from
the group consisting of ammonium lauryl sulfate, ammonium lauryl ether sulfate (varying degrees of ethoxylation), ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

* * * * *